(12) United States Patent
Lee et al.

(10) Patent No.: US 9,138,748 B2
(45) Date of Patent: Sep. 22, 2015

(54) REACTION VESSEL COMPRISING CONDUCTIVE LAYER AND INNER NON-METALLIC LAYER

(75) Inventors: Martin Alan Lee, Wiltshire (GB); David James Squirrell, Wiltshire (GB); Ross Peter Jones, Cambridge (GB); Roger James Williamson, Hertfordshire (GB); George Richard Gregory, Hertofrshire (GB); Graham Gutsell, Wiltshire (GB)

(73) Assignee: ENIGMA DIAGNOSTICS LIMITED (GB)

( * ) Notice: Subject to any disclaimer, the term of this patent is extended or adjusted under 35 U.S.C. 154(b) by 1344 days.

(21) Appl. No.: 12/671,272

(22) PCT Filed: Aug. 1, 2008

(86) PCT No.: PCT/GB2008/002631
§ 371 (c)(1),
(2), (4) Date: Jul. 29, 2010

(87) PCT Pub. No.: WO2009/019454
PCT Pub. Date: Feb. 12, 2009

(65) Prior Publication Data
US 2010/0297707 A1 Nov. 25, 2010

(30) Foreign Application Priority Data
Aug. 3, 2007 (GB) .................................. 0715170.7

(51) Int. Cl.
| C12P 19/34 | (2006.01) |
| C12M 1/00 | (2006.01) |
| B01L 7/00 | (2006.01) |
| B01L 3/00 | (2006.01) |
| G01N 21/03 | (2006.01) |

(52) U.S. Cl.
CPC ............... *B01L 7/52* (2013.01); *B01L 3/50851* (2013.01); *B01L 2300/0858* (2013.01); *B01L 2300/0887* (2013.01); *B01L 2300/16* (2013.01); *B01L 2300/1827* (2013.01); *B01L 2300/1883* (2013.01); *G01N 21/0332* (2013.01)

(58) Field of Classification Search
None
See application file for complete search history.

(56) References Cited

U.S. PATENT DOCUMENTS 3,342,754 A   9/1967   Gorham
3,343,754 A   9/1967   Klein et al.
(Continued)

FOREIGN PATENT DOCUMENTS

CA   20927442 C   8/2001
EP   0263753 A1   4/1988
(Continued)

OTHER PUBLICATIONS

Young et al, "PDMS-based micro PCR chip with Parylene coating", J. Micromech. Microeng.13 (2003) 768-774 (8 pages).
(Continued)

*Primary Examiner* — Jill Warden
*Assistant Examiner* — Julie Tavares (57) ABSTRACT

A reaction vessel for conducting a chemical or biochemical reaction, such as a polymerase chain reaction wherein at least one wall of said vessel comprises a metallic layer and an inner non-metallic layer. Reaction systems comprising combinations of vessels of the invention and apparatus for heating them, as well as particular reactions vessels are also described and claimed.

28 Claims, 5 Drawing Sheets

(56) References Cited

U.S. PATENT DOCUMENTS

| | | | |
|---|---|---|---|
| 3,614,434 A | 10/1971 | Horwitz et al. | |
| 4,475,411 A | 10/1984 | Wellerfors | |
| 4,928,539 A | 5/1990 | Champseix et al. | |
| 5,279,796 A | 1/1994 | Parker et al. | |
| 5,364,790 A | 11/1994 | Atwood et al. | |
| 5,527,510 A | 6/1996 | Atwood et al. | |
| 5,669,524 A | 9/1997 | Loedel | |
| 5,681,741 A | 10/1997 | Atwood et al. | |
| 5,720,923 A | 2/1998 | Haff et al. | |
| 5,738,920 A * | 4/1998 | Knors | 428/35.9 |
| 5,779,977 A | 7/1998 | Haff et al. | |
| 5,827,480 A | 10/1998 | Haff et al. | |
| 5,856,174 A | 1/1999 | Lipshutz et al. | |
| 5,860,976 A | 1/1999 | Billings et al. | |
| 5,960,976 A * | 10/1999 | Tsuno | 220/62.22 |
| 6,015,534 A | 1/2000 | Atwood | |
| 6,016,712 A | 1/2000 | Warden et al. | |
| 6,024,703 A | 2/2000 | Zanelli et al. | |
| 6,033,880 A | 3/2000 | Haff et al. | |
| 6,190,617 B1 | 2/2001 | Clark et al. | |
| 6,228,657 B1 | 5/2001 | Genovese | |
| 6,281,008 B1 | 8/2001 | Komai et al. | |
| 6,312,886 B1 | 11/2001 | Lee et al. | |
| 6,361,958 B1 | 3/2002 | Shieh et al. | |
| 6,391,541 B1 | 5/2002 | Petersen et al. | |
| 6,500,622 B2 | 12/2002 | Bruchez, Jr. et al. | |
| 6,635,471 B1 | 10/2003 | Lee et al. | |
| 6,706,519 B1 * | 3/2004 | Kellogg et al. | 435/287.2 |
| 6,787,338 B2 * | 9/2004 | Wittwer et al. | 435/91.2 |
| 6,838,243 B2 | 1/2005 | Lai et al. | |
| 6,942,771 B1 | 9/2005 | Kayyem | |
| 6,958,217 B2 | 10/2005 | Pedersen | |
| 6,973,718 B2 | 12/2005 | Sheppard, Jr. et al. | |
| 7,112,587 B2 | 9/2006 | Timmer et al. | |
| 2001/0029793 A1 | 10/2001 | Moler et al. | |
| 2001/0049134 A1 | 12/2001 | Lee et al. | |
| 2002/0050456 A1 | 5/2002 | Sheppard et al. | |
| 2002/0094584 A1 | 7/2002 | Shieh et al. | |
| 2003/0215816 A1 | 11/2003 | Sundararajan et al. | |
| 2004/0259237 A1 | 12/2004 | Kellogg et al. | |
| 2005/0059161 A1 | 3/2005 | Anderson et al. | |
| 2005/0227983 A1 | 10/2005 | Timmer et al. | |
| 2005/0259237 A1 | 11/2005 | Wu | |
| 2006/0024211 A1 | 2/2006 | Giter et al. | |
| 2006/0073600 A1 | 4/2006 | Kitamura | |
| 2006/0204699 A1 | 9/2006 | Maltezos et al. | |
| 2006/0266402 A1 | 11/2006 | Zhang et al. | |
| 2007/0026439 A1 | 2/2007 | Faulstich et al. | |
| 2007/0036687 A1 * | 2/2007 | Woods et al. | 422/102 |
| 2007/0059692 A1 | 3/2007 | Gao et al. | |
| 2007/0080062 A1 | 4/2007 | Harnett et al. | |
| 2007/0171257 A1 | 7/2007 | Yang et al. | |
| 2007/0292941 A1 | 12/2007 | Handique et al. | |

FOREIGN PATENT DOCUMENTS

| | | | |
|---|---|---|---|
| EP | 1752222 A1 | 2/1997 | |
| EP | 0814114 A1 | 12/1997 | |
| EP | 1113271 A2 | 4/2001 | |
| EP | 1113271 A | 7/2001 | |
| EP | 1113271 A2 * | 7/2001 | |
| EP | 1557672 A | 7/2005 | |
| EP | 0636413 A2 | 6/2006 | |
| EP | 1752222 A1 | 2/2007 | |
| GB | 2333250 A | 7/1999 | |
| GB | 2357288 A | 6/2001 | |
| GB | 2404883 A * | 2/2005 | |
| GB | 2424199 B | 6/2007 | |
| GB | 2424380 B | 6/2007 | |
| GB | 2424381 B | 6/2007 | |
| GB | 2404883 B | 2/2008 | |
| GB | 2441833 A | 3/2008 | |
| JP | 2003-164279 A | 6/2003 | |
| JP | 2004150805 A | 5/2004 | |
| JP | 2005296017 A | 10/2005 | |
| WO | WO98/24548 A1 | 6/1998 | |
| WO | WO9824548 A | 6/1998 | |
| WO | WO9857180 A1 | 12/1998 | |
| WO | WO9904239 A2 | 12/1998 | |
| WO | WO9930823 A | 6/1999 | |
| WO | WO99/33559 A1 | 7/1999 | |
| WO | WO9933559 A | 7/1999 | |
| WO | WO01/41931 A2 | 6/2001 | |
| WO | WO01/87768 A2 | 11/2001 | |
| WO | WO0187768 A2 | 11/2001 | |
| WO | WO2004/045772 A2 | 6/2004 | |
| WO | WO2004045772 A2 | 6/2004 | |
| WO | WO2004/055522 A1 | 7/2004 | |
| WO | WO2004054715 A1 | 7/2004 | |
| WO | WO2005011834 A | 2/2005 | |
| WO | WO2005019836 A2 | 3/2005 | |
| WO | WO2005059929 A2 | 6/2005 | |
| WO | WO2005080606 A1 | 9/2005 | |
| WO | WO2006024879 A1 | 3/2006 | |
| WO | WO2006027757 A2 | 3/2006 | |
| WO | WO2006042826 A1 | 4/2006 | |
| WO | WO2006/130408 A2 | 12/2006 | |
| WO | WO2007054747 A1 | 5/2007 | |
| WO | WO2007/082466 A1 | 7/2007 | |
| WO | WO2007138302 A | 12/2007 | |
| WO | WO2007138302 A1 | 12/2007 | |
| WO | WO2008006617 A | 1/2008 | |
| WO | WO2008065423 A1 | 6/2008 | |
| WO | WO2009019452 A1 | 2/2009 | |
| WO | WO2009019450 A1 | 12/2009 | |

OTHER PUBLICATIONS

C.A. Harper, ed., Handbook of Plastics and Elastomers, p. 1-82ff, McGraw-Hill, NY, 1975 (3 pages).

Parylene and NOVA TRAN® World-Class Parylene Coating Services', product brochure, Specialty Coating Systems/Alpha Metals, Inc., 1995 (6 pages).

Parylene Conformal Coatings Specifications and Properties', product brochure, Specialty Coating Systems/Alpha Metals, Inc., 1997 (12 pages).

W. Leventon, Coatings Cover Many Bases for Device Makers. MedicalLink.com, Medical Device and Diagnostic Industry, dated 2007 (3 pages).

Search report for Application No. GB0715170.7 dated Nov. 22, 2007 (4 pages).

Search report for Application No. GB0715169.9 dated Dec. 5, 2007 (5 pages).

Shin, Y, PDMS-based micro PCR chip with Parylene coating, Institute of Physics Publishing, Journal of Micromechanics and Microengineering, J. Micromech, Microeng. 13 (2003) 768-774 (7 pages).

International Search Report for PCT/GB2008/002629 (International Publication No. WO2009/019452A1) dated Nov. 6, 2008 (5 pages).

International Search Report for PCT/GB2008/002631 (International Publication No. WO2009/019454A1) dated Nov. 24, 2008 (4 pages).

International Search Report for PCT/GB2008/002627 (International Publication No. WO2009/019450A1) dated Nov. 14, 2008 (4 pages).

Office Action issued Jun. 20, 2012 for U.S. Appl. No. 12/671,839 (21 pages).

Office Action issued Nov. 25, 2011 for U.S. Appl. No. 12/671,839 (22 pages).

Office Action issued Mar. 28, 2011 for U.S. Appl. No. 12/671,257 (22 pages).

Parylene and NOVA TRAN® World-Class Parylene Coating Services', product brochure, Specialty Coating Systems/Alpha Metals, Inc., 1995 (18 pages).

Office Action issued May 1, 2012 for U.S. Appl. No. 12/671,777 (5 pages).

Final Office Action issued Sep. 26, 2012 for U.S. Appl. No. 12/671,777 (21 pages).

* cited by examiner

REACTION VESSEL COMPRISING CONDUCTIVE LAYER AND INNER NON-METALLIC LAYER

The present invention relates to reaction vessels useful in chemical and biochemical reactions which are required to undergo controlled heating and/or cooling, in particular, vessels which are required to undergo thermal cycling, where a sequence of different temperatures are required.

A particular example of such a reaction are a number of nucleic acid amplification methods, in particular the polymerase chain reaction (PCR). As is well known, in this reaction, exponential amplification of nucleic acids is achieved by cycling the sample containing or suspected of containing the target nucleic acid through an iterative sequence of different temperatures in the presence of specifically designed primer sequences and polymerase enzymes able to extend those primer sequences. These temperatures represent the temperatures necessary for nucleic acid denaturation (and generally requires temperatures of about 95° C.), primer annealing (at a lower temperature for example at about 55° C.) and primer extension (which may require and intermediate temperature for example of about 74° C.)

There is frequently a need to obtain the results of a PCR reaction quickly, for example in cases of environmental contamination which may be the result of hostile activity. However, even in a clinical or diagnostic situation, the production of quick results can be helpful, in particular where patient compliance or return can be problematic.

Clearly, for fast PCR, the sample must be rapidly heated and cooled. This is facilitated by making the sample small to reduce its thermal mass and by minimising the distances over which heat must be transferred. The same considerations must be applied to the container of the sample.

Thus, a number of examples of apparatus designed to carry out PCR reactions utilize reaction vessels which comprise a capillary tube format (ie long and thin WO 2005/019836) or as a planar structure (flat and thin) (WO2006024879), the content of which are incorporated herein by reference.

A variety of heating systems are utilized in order to achieve rapid PCR. These include for example fluid based systems in which hot fluid such as air is fed to the container of the sample for heating purposes, and non-heated fluid is supplied to effect cooling (see for example U.S. Pat. No. 6,787,338 and WO2007/054747, the content of which is incorporated herein by reference).

In an alternative type of apparatus, electrically conducting polymer (ECP) is used as both the heating element and in some cases also the container (see WO 98/24548, the content of which is also incorporated herein by reference).

The ECP acts as a resistive heater and so it is required to be connected to an electrical supply by way of electrical connections. As an inevitable consequence of reducing the thermal mass of the sample and facilitating heat transfer into and out of it, the means of connecting and locating the ECP can have significant thermal effects upon it.

A particular problem is the formation of temperature gradients as heat can be conducted both out from and in to the extremities of the ECP tube, through the electrical connections, as it is heated and cooled, respectively.

This problem has been addressed in some instances by examining the electrical connections themselves and in particular, the mountings for the electrodes. These must be electrically insulating and are preferably also thermally insulating. However, the property of thermal insulation is in itself insufficient.

Electrical connectors (or electrodes) that are thermally insulating heat and cool slowly which has the effect of making them important contributors to the formation of longitudinal temperature gradients during rapid thermal cycling. The mountings must also therefore have a low thermal mass as well as being thermal insulators. This may be achieved by placing insulating materials that have been structured to reduce their thermal mass whilst retaining the physical integrity needed to support the electrodes. Such structuring, in its essence, requires the inclusion of air gaps in the mountings. This may be achieved by using foam materials, such a honeycomb or reticulated foam to form a mount for the electrode. The mounts are suitable in the form of a pillared or corrugated mount for the electrical connector (as described for example in WO2005/0011834, WO2004/045772 and copending British Patent Application No. 0623910.7).

In PCR, it would be ideal to have all parts of the sample at the same controlled temperature all of the time. This is extremely difficult in a system that is being rapidly heated and cooled. In the capillary format, both radial and longitudinal temperature gradients are formed.

The applicants have found however that by utilizing highly thermally conducting layers such as metallic layers in walls of reaction vessels such as those used for PCR, these gradients may be reduced.

According to the present invention there is provided a reaction vessel for conducting a chemical or biochemical reaction, wherein at least one wall of said vessel comprises a layer of a highly thermally conducting material, (in particular a metallic layer) and an inner non-metallic layer. Preferably the said reaction vessel comprises a capillary vessel or a flattened capillary vessel.

For the avoidance of doubt, the term "layer" as used herein refers to any essentially laminar arrangement of material, including both self-supporting layers as well as coatings. Layers or coatings which are not self supporting, will generally conform to the shape of the relevant substrate, and so for example may in practice may be any shape, including in particular tubular. Similarly, self-supporting layers may take whatever form is particularly convenient in relation to the context in which they are used.

Reaction vessels of the invention have good thermal conductivity as a result of the presence of the highly thermally conducting layer of the wall, and therefore can be used in reactions where temperature control, or in particular temperature cycling with good temperature uniformity is important. Therefore, they may be particularly useful in reactions such as nucleic acid amplification reactions which involve thermal cycling such as the polymerase chain reaction (PCR). The good thermal conductivity means that significant temperature gradients through the vessel do not form, or are rapidly evened out if they do occur, so that the temperature profile along and across the sample is made flatter (more homogeneous).

Generally, metal walled vessels have not be used hitherto in reaction vessels because they are generally chemically reactive in particular with biological molecules such as nucleic acids and proteins, and so the metal interferes with reagents in the vessel and so disrupts the reaction. However, the applicants have found that this problem can be overcome by the provision of an inner non-metallic layer, in contact with the thermally conducting layer such as the metallic layer so as to effectively form a composite.

The vessel is suitably an elongate vessel, with the layered wall forming at least one of the long walls so as to increase the surface area of the metal containing wall which is in the proximity of a reagent in the vessel. In particular, the vessel is a capillary vessel or a flattened capillary vessel, where the length is selected to accommodate the volume of the sample and inner diameters are small. In particular, the inner diameter of a capillary tube is in the range of from 0.2 to 2 mm. The thickness of the wall is generally from about 0.1 to about 1.5 mm.

Examples of such vessels are described for example in WO2004/054715, U.S. Pat. No. 6,015,534 and WO 2005/019836, the content of which is incorporated herein by reference.

Such vessels effectively comprise a single radial side wall and this suitably comprises a metallic layer over substantially all, and preferably all its area.

Where flattened tubes are used, they may be of a shape described in WO2006024879, the content of which is incorporated herein by reference. Specifically, such vessels have a width:depth ratio of about 2:1 or more, for example, of 3:1 or more. Typically the width of the vessels may be of the order of 1 mm or less for example 0.8 mm or less, whereas the depth is generally 0.5 mm or less, and suitably less than 0.3 mm. The vessels may be tapered.

In these cases, at least one side wall comprises a metallic layer, and preferably all side walls comprise a metallic layer. The lower wall may also have this construction, although in many instances, it is preferred that the lower wall, which forms the base of the vessel is of a transparent material such as glass or a transparent polymer, such as polycarbonate so that the contents of the reaction vessel can be optically monitored during the reaction. The transparent material must have a reasonably high melting point to withstand the heat applied by the ECP. Preferably a seal is provided between the transparent material and the capillary vessel or flattened capillary vessel. A suitable seal would be an O-ring, which may be integral with or separate to the transparent material.

This is particularly helpful in the case of the use of the so-called "real-time" PCR reactions where optical signals, in particular fluorescent signals from signalling reagents added to the PCR reaction, produce a variable signal as the reaction progresses, so that the progress of the reaction can be monitored. Such monitoring gives rise to the option of quantifying the amount of target nucleic acid within the initial sample, so providing further information which may be of use, for example in diagnostics, in determining the seriousness of a particular condition.

Suitable non-metallic materials for the inner non-metallic layers may include polymeric materials or glass or even a passivated layer created through anodisation of a metal, or similar process, or combinations of these. In particular, however, the inner non-metallic layer is a polymer or glass or combination of these.

In a particular embodiment, the inner non-metallic layer is a glass layer, since glass is generally well recognised as being compatible with many biochemical and chemical reactions including the polymerase chain reaction.

However, polymeric materials such as polyurethane, polyethylene, polypropylene, or polycarbonates, as well as silicones which are compatible with the sample and with the particular reaction being carried out within the reaction vessel.

Such inner layers will generally be rigid and supporting structures, which may be formed by processes such as injection or extrusion moulding and the like. These may then be coated with a metallic layer, or they may be extruded or formed directly onto the metallic layer.

However, if necessary or required a thin layer for example of polymeric material may deposited on the metallic layer for example using techniques such as vapour deposition, liquid phase deposition or plasma polymerisation to provide a relatively thin layer which may itself constitute the inner non-metallic layer. Alternatively, such a thin layer may be applied to a different inner non-metallic layer as described above to form a composite structure.

A particularly suitable polymeric layer of this type is formed of parylene or derivatives thereof. Parylene is a generic name applied to polyxylylene as for example as described in U.S. Pat. No. 3,343,754, the content of which is incorporated herein by reference.

Compounds of this type can be represented by the general formula (I)

where is R is a substituent group, m is 0 or an integer of from 1 to 3 and n is sufficient for the compound to be a polymer.

Where m is greater than 1, each R group may be the same or different.

In one embodiment, m is 0.

Suitable substituent groups R include but are not limited to $R^1$, $OR^1$, $SR^1$, $OC(O)R^1$, $C(O)OR^1$, hydroxyl, halogen, nitro, nitrile, amine, carboxy or mercapto and where $R^1$ is any hydrocarbon group and where $R^1$ may be optionally substituted by one or more groups selected from hydroxyl, halogen, nitro, nitrile, amine or mercapto.

Suitable hydrocarbon groups include alkyl groups such as straight or branched chain $C_{1-10}$alkyl groups, alkenyl groups such as straight or branched $C_{2-10}$alkenyl groups, alkynyl groups such as straight or branched $C_{2-10}$alkynyl groups, aryl groups such as phenyl or napthyl, aralkyl groups such as aryl($C_{1-10}$)alkyl for instance benzyl, $C_{3-10}$cycloalkyl, $C_{3-10}$cycloalkyl($C_{1-10}$)alkyl, wherein any aryl or cycloalkyl groups may be optionally substituted with other hydrocarbon groups and in particular alkyl, alkenyl or alkynyl groups as described above.

Particular examples of groups R include alkyls such as methyl, ethyl, propyl, butyl or hexyl, which may be optionally substituted with hydroxy, halo or nitrile such as hydroxymethyl or hydroxyethyl, alkenyls such as vinyl, aryls in particular phenyl or napthyl which may be optionally substituted by halo or alkyl groups such as halophenyl or $C_{1-4}$alkylphenyl, alkoxy groups such as methoxy, ethoxy, propoxy, carboxy, carbomethoxy, carboethoxy, acetyl, propionyl or butyryl.

In particular, R is selected from halogen (particularly chlorine or bromine), methyl, trifluoromethyl ethyl, propyl, butyl, hexyl, phenyl, $C_{1-4}$alkylphenyl, naphthyl, cyclohexyl and benzyl.

Examples of such polymers are sold as "Parylene". Particular variety of parylene which may be obtained include Parylene N (where m is 0), Parylene C (where m is 1 and R is chloro), Parylene F (where m is 1 and R is trifluoromethyl) and Parylene D (where m is 2 and each R is chloro).

Parylene is a particularly convenient polymeric material for providing an internal coating for the metallic surface, as it may be readily applied using a vapour deposition process. In this process a solid dimer of formula (II)

(II)

where R and m are as defined above, is placed into a suitable vaporisation chamber in solid form. When the chamber and heated under reduced pressure, for example to temperatures of about 150° C. at low pressure, for example of about 1 mmHg, the dimer vapourises. The vapour is then transferred into a pyrolysis chamber where the temperature is much higher, for example at about 650° C. and the pressure is for example of 0.5 mmHg, Pyrolysis occurs so as to cause the formation of a reactive monomeric species of formula (III).

(III)

If this is allowed to pass into a further chamber containing the item to be coated which is at ambient temperature, but also at low pressure, for example of 0.1 mmHg, polymerisation of the species (III) occurs on the surface of the object, so that a coating of the polymer of formula (I) above is produced.

The species (III) condenses on the surface in a polycrystalline fashion, providing a coating that is conformal and pinhole free. This is important to ensure that any sample within the reaction vessel is isolated from the metallic layer.

Compared to liquid processes, the effects of gravity and surface tension are negligible—so there is no bridging, thinout, pinholes, puddling, run-off or sagging. And, since the process takes place at room temperature, there is no thermal or mechanical stress on the object.

Parylene is physically stable and chemically inert within its usable temperature range, which includes the temperatures at which PCR reactions are conducted. Parylene also provides excellent protection from moisture, corrosive vapours, solvents, airborne contaminants and other hostile environments.

It is widely used in the electronics industry to coat and protect electronic components. However, the applicants are the first to find that parylene is compatible with chemical or biochemical reactions and in particular with the PCR reaction, and the use of parylene for coating reaction vessels and in particular PCR reaction vessels is described and claimed in the applicants copending patent application of even date.

In the vessel of the apparatus, the metallic layer effectively forms a thermal shunt, conducting heat rapidly from one part of the reaction vessel to another. Thus it minimises the build-up of thermal gradients in the vessel and therefore in the sample during the reaction, which is important in ensuring that the reaction proceeds efficiently and well.

Thus vessels comprising a highly thermally conducting material most suitably comprise a material which has a thermal conductivity in excess 15 W/mK. Materials having this property will generally be metallic in nature, but certain polymers, in particular those known as "cool polymers" or polymers containing thermally conducting ceramics such as boron nitride as well as diamond, may have the desired level of thermal conductivity. In particular however, the highly thermally conducting material is metallic, which may be of any suitable metal or metal alloy including aluminium, iron, steel such as stainless steel, copper, lead, tin or silver. In particular, the metallic layer comprises aluminium. Use of a metal or metal alloy has the additional advantage of giving rigidity to the sample vessel.

The thickness of the highly thermally conducting material is preferably chosen to meet the general requirement t·λ>0.11 W/K, where t is the wall thickness of the thermal short and λ is the thermal conductivity. This combination ensures good thermal uniformity in the sample within the stalk. Aluminium has a thermal conductivity λ of 237 W/mK and a suitable wall thickness is 0.5 mm. In this case t×λ=0.005×237=0.1185 W/K, which meets the requirement above.

The reaction vessel in accordance with the invention, may be heated by any suitable heating means, and as a result of the presence good thermal conductivity of the walls of the vessel due to the presence of the highly thermally conducting layer, the heat will be readily transferred to the vessel contents.

Thus the vessels are suitable for use in a wide range of apparatus in particular thermal cycling equipment. These may be heatable and/or coolable using a number of different technologies, including the use of fluid heaters and coolers such as air heaters and coolers in particular those heated by halogen bulbs, as described for example in U.S. Pat. No. 6,787,338 and WO2007/054747, the content of which is incorporated by reference, as well as in vessels using ECP as resistive heating elements, for example as described in WO 98/24548 and WO 2005/019836 as will be discussed further below. The vessels may also be used in more conventional devices such as solid block heaters that are heated by electrical elements or induction heaters that induce currents in the metallic layer. For cooling the apparatus may incorporate thermoelectric devices, compressor refrigerator technologies, forced air or cooling fluids as necessary. However, where the vessels of the invention comprise a metallic layer, this means that they may also be capable of being heated using for example induction methods. Apparatus used to heat vessels of the invention in this way will have the facility to heat the vessel by electromagnetic induction, for example by using a high-frequency alternating current (AC) to induce eddy currents within the metal. Resistance of the metal to these currents leads to Joule heating of the metal. Heat is also generated by magnetic hysteresis losses. For use in induction heating apparatus, it will be clear that the metallic layer within the vessel should be of a suitable material to allow it to be heated in this way, and so for example iron metallic layers may be preferred to say stainless steel or copper.

Reaction systems comprising combinations of reaction vessels as described above, and apparatus which is able to accommodate said reaction vessel, and which comprises a heating system adapted to controllably heat and cool said vessel, in particular using any of the methods discussed above, form a further aspect of the invention. The apparatus may be able to accommodate multiple reaction vessels.

When the reaction vessels of the invention are utilised in combination with resistive heating elements, such as ECP, it is necessary to ensure that where the highly thermally conducting layer is also electrically conducting, such as a metallic layer, this is electrically insulated from the resistive heater in order to prevent short circuits etc. The applicants have found that it is possible to passivate the surface of a metal layer so that it is electrically isolated from the ECP, but still in good thermal contact. For example in the case of an aluminium metallic layer, anodisation of any surface of the aluminium layer which is to be in contact with the resistive heater such as the ECP provides such insulation.

Alternatively, a parylene layer, preparable as described above may be applied to the surface of the highly thermally conducting layer such as the metallic layer which contacts the ECP so as to provide an effective eletically insulating layer. Such layers have the benefit that they do not significantly add to the size or thermal mass of the vessel.

The ECP is suitably arranged as a sheath or coating arranged outside the highly thermally conducting layer and the electrically insulating layer thereof, as described in WO 98/24548. By keeping the elements of the reaction vessel small, in particular as thin layers, the thermal mass of the vessel remains low, and so fast heating and cooling can take place as is required for rapid PCR.

Thus in a particularly preferred embodiment, a wall of the reaction vessel, and suitably the entire side walls of the vessel comprise an inner non-metallic layer, for example of glass or a polymeric material. This is covered by a metallic layer as described above, which is itself covered by an electrically insulating layer, for example a layer of anodised aluminium or parylene or a derivative thereof as described above. Outside of this layer is suitably provided a layer of electrically conducting polymer. Such vessels are generally intended to be disposable after a single use.

In another preferred embodiment, a wall of the reaction vessel, and suitable the entire side walls of the vessel comprise a metallic layer, for example aluminium. This is covered by an electrically insulating layer, for example a layer of anodised aluminium or parylene or a derivate thereof as described above. Outside of this layer is suitably provided a layer of electrically conducting polymer.

Thermal lag is reduced by keeping the ECP in intimate contact with the highly thermally conducting layer, (i.e. avoiding air gaps). Thermal lag is further reduced by providing no inner layer to the highly thermally conducting layer with the exception of the parylene coating which has minimal effect as a thermal insulator because it is so thin (about 5 micrometres).

The electrically conducting polymer needs to be connected to an electrical supply, and so electrical connections, which may be integral with the vessel, are suitably provided at each end of the ECP.

The ECP elements used in the vessels as resistive heating elements can be manufactured by various processes, but most a convenient process involves injection moulding of the polymer. However, in the process of injection moulding, the material tends to form an outer polymer-rich skin that may creates at least a partial electrically insulating barrier to any external means of making electrical contact.

In such cases, the applicants have found that it is helpful to break through the insulating skin and make electrical contact with the bulk material in order to increase the efficiency of the heating system.

Thus, in a particular embodiment, the reaction vessel as described above, is connectable to an electricity supply by means of barbed electrical contacts which pierce the surface of the electrically conducting polymer. These are suitably integral with the vessel.

Such barbed connectors may take various forms depending upon the particular configuration of the reaction vessel itself. In particular, where the vessel is of a generally tubular configuration, suitable barbed connectors may take the form of annular metal rings with inwardly projecting barbs or the like, similar in design to "Starlock Washers".

The inwardly projecting barbs will cut through the insulating skin to make electrical contact with the bulk conducting material, as well as hold the ring in position. The outer portion will present a metallic surface for electrical interconnection, and so apparatus intended to accommodate the vessels will be configured appropriately.

Furthermore, the barbs provide effectively a scalloped edge which helps to reduce the size and therefore the thermal mass of the connectors and also, reduces the contact area with the ECP. This has the further advantage of further minimising heat exchange between the electrical connectors and the ECP, so further assisting in reducing unwanted thermal gradient formation.

The connectors and particularly the barbs thereof, are suitably constructed of a material which have high mechanical strength, so that the barbs can be sharpened to enhance the penetration ability. Whilst many metals are able to fulfill this function, a particularly suitable material for the connectors has been found to be stainless steel. This not only has the required mechanical strength and electrical conductivity, but also, it has a high corrosion resistance, at 16 W/mK, a surprisingly low thermal conductivity compared to many other metals (cf Copper @ 399 W/mK, Aluminium @ 237 W/mK). By using this material, and by designing the connectors so that their area is as small as possible, helps to reduce unwanted thermal effects at the electrodes.

Connections of this type are cost effective to manufacture, which will be a particular advantage in cases where the proposed PCR vessel is to be a high volume disposable item.

They may, in fact, be used in connection with any reaction vessel or device which includes ECP as a resistive heater, and such reaction vessels and devices form a further aspect of the invention.

In one embodiment, the profile of the ECP may itself be adjusted to vary its radial thickness so that the resistance heating is distributed unevenly in a way so as to reduce gradients. This may be done empirically, in relation to any particular vessel type, by determining the gradient profile which occurs and adjusting the thickness of the ECP in various regions of the vessel accordingly. Typically, the profile will be tapered, being narrower at the bottom of the vessel than the top.

Such modifications may be included in vessels which include or utilise ECP resistance heaters, irrespective of the presence or otherwise of the highly thermally conducting layer, and such vessels form yet a further aspect of the invention.

As discussed briefly above, the apparatus into which the vessel is accommodated for use suitably is provided with mounts of a material which is both an electrical and thermal insulator (i.e the material absorbs and releases heat slowly) and also have a low thermal mass. This can be achieved by making the electrode mounts "air-like" ie formed as foam, skeletal or honeycomb structures. However they must be able to physically support and position the electrodes, and therefore they must have a degree of rigidity, firmness and/or resilience.

Thus in a particular embodiment of the apparatus for thermally cycling the contents of the reaction vessel as described above comprises a solid foam material arranged in direct contact with at least one of said electrical contacts.

The solid foam material acts as an insulator, preventing heat flows and particularly heat loss through the electrical contacts. As a result, a more uniform temperature can be maintained within the reaction vessel. By utilising specifically a solid foam in preference to a conventional solid insulator, such as a solid plastics insulator, the performance of the apparatus is significantly enhanced. Thermal gradients set up within the reaction vessel can be further reduced.

It is believed that this is due to the fact that foam-like materials have a lower thermal mass than solids. Therefore, in addition to providing insulation preventing the flow of heat into and out of the reaction vessel through the electrical contact, they do not significantly hinder the heating and cooling process.

In contrast, solid insulators with significant thermal mass were found to heat up and cool down slowly (rather than not at all), thereby acting as sources or sinks of heat depending on their temperature relative to the sample. This was found to be disadvantageous in this context.

Suitable solid foam materials include metal, glass, carbon, polymer, ceramic foams or composites made of several of these.

Particular examples of such foam materials are polymeric foams such as polyurethane or polystyrene foams.

In a particular embodiment, the foam material is a ceramic foam. Ceramic foams generally comprise inorganic, non-metallic materials (such as metal oxides, silicides, nitrides, carbide or borides) with a crystalline structure, which have usually been processed at a high temperature at some time during their manufacture.

Many such foams are now commercially available. They have been developed mainly for the aerospace industry where their utility as insulators is a result of their light weight.

Solid foams generally comprise solids which have many gas bubbles trapped within them. They may be rigid or pliable in nature, but are preferably rigid so as to support the electrical contacts. Where they are pliable, the foam material suitably has a good "shape memory".

Various forms and types of solid foam materials are known. Some are known as "refractory" foams. They are made by various methods depending upon the nature of the material used. For instance, solid foams comprising polymers may be readily prepared including foaming agents into the preparation process, as is well understood in the art. Syntactic foams and self-foamed materials such as foam glass may be prepared in a similar way.

Other solid foams may utilise a foamed polymer as the basic starting material and materials are essentially coated onto these or onto carbonaceous skeletons formed by pyrolysis of the polymer foam. For example, ceramic foams can be produced by coating a polymer foam or a carbon skeleton derived from it, with an appropriate binder and ceramic phases, and then sintering at elevated temperatures. Metallic foams may be formed by electrolytically depositing the metal onto a polymer foam, utilizes an electrodeless process for the deposition of a metal onto the polymer foam precursor via electrolytic deposition.

Suitably the solid foam material is of a material, which has no fluorescent or phosphorescent properties, even when illuminated with a light source. This means that it may not interfere with the fluorescent signalling or labelling systems that are frequently utilised for detecting the products of an amplification reaction. Such systems may be used to detect the product of amplification either at the end point of the reaction, or, increasingly, in "real-time" as the reaction progresses. These systems, which include the well known "Taqman™" system as well as other systems such as those described for example in Homogeneous fluorescent chemistries for real-time PCR. Lee, M. A., Squirrell, D. J., Leslie, D. L. and Brown, T. in *Real-time PCR: an essential guide*, J. Logan, K. Edwards & N. Saunders eds., Horizon Scientific Press, Wymondham, p. 31-70, 2004, the content of which is incorporated herein by reference. For instance, generic methods utilise DNA intercalating dyes that exhibit increased fluorescence when bound to double stranded DNA species. Fluorescence increase due to a rise in the bulk concentration of DNA during amplifications can be used to measure reaction progress and to determine the target molecule copy number. Furthermore, by monitoring fluorescence with a controlled change of temperature, DNA melting curves can be generated, for example, at the end of PCR thermal cycling.

However, when the material has a degree of fluorescence, this may be obviated by dying, coating or inking the foam before use.

The solid foam material is arranged in contact with at least one and preferably both of the electrical contacts. Suitably sufficient foam material is arranged so that in use, it effectively isolates the electrical contacts from environmental effects. This will generally be achieved by arranging the solid foam material in contact with at least the remote edges of the electrical contacts.

If desired, a solid insulator material may also be provided and arranged to contact the solid foam material.

Suitable solid insulator materials are well known in the art, and include polymeric or fibrous materials. In particular the solid insulator is a polymeric insulator such as an acetal homopolymer resin such as Delrin™, acrylonitrile-butadiene-styrene terpolymer (ABS) or polytertrafluroethylene (PTFE).

The solid insulator may be arranged to contact a substantial portion, for example at least one side of the solid foam material. This additional insulation will protect the solid foam material itself from changes in environmental temperature and so enhance the overall reliability of the system. Suitably the additional solid insulator is provided so as to effectively isolate the reaction vessel from the external environment when in use. The precise arrangement of the solid insulator therefore will vary depending upon the nature of the reaction vessel and the manner in which it is used.

As mentioned above, example of mounts which include foam-like materials are described for example in WO2005/0011834, WO2004/045772, where the foam materials have a degree of resilience or compliance to allow them to hold the connectors firmly, or co-pending British Patent Application No. 0623910.7, where firm foam-like materials may be used, which are sprung-loaded to ensure that a sufficiently firm hold on the connectors is achieved.

In an alternative embodiment, the apparatus into which the vessel is accommodated for use is provided with mounts of low thermal mass by providing one or more low volume mounts of solid insulator material. Suitable solid insulator materials are well known in the art, and include polymeric or fibrous materials. In particular the solid insulator is a polymeric insulator such as an acetal homopolymer resin such as Delrin™, acrylonitrile-butadiene-styrene terpolymer (ABS) or polytertrafluroethylene (PTFE). In a preferred embodiment, three low volume mounts of solide insulator material are provided to support the vessel.

The apparatus may be provided with electrical contacts for connection to the electrical connectors of the vessel. The electrical contacts may be sprung contacts, which have the advantage of low volume, reducing the thermal mass. One or more electrical contacts may be integral with the one or more mounts.

Reaction vessels as described above and reaction systems comprising them can be used in chemical and biochemical reactions as required. Thus, in a further aspect, the invention provides a method for carrying out a chemical or biochemical reaction which requires at least one heating step, said method comprising placing chemical or biochemical reagents into a reaction vessel as described above, and heating said reagents so as to bring about said chemical or biochemical reaction. In particular, the vessel is positioned into apparatus specifically designed to hold it, and to heat and/or cool it as required. In particular, the apparatus comprises a thermal cycler as described above, and the reaction requires thermal cycling, in particular is a polymerase chain reaction.

The invention will now be particularly described by way of example with reference to the accompanying diagrammatic drawings in which.

Figure 1:
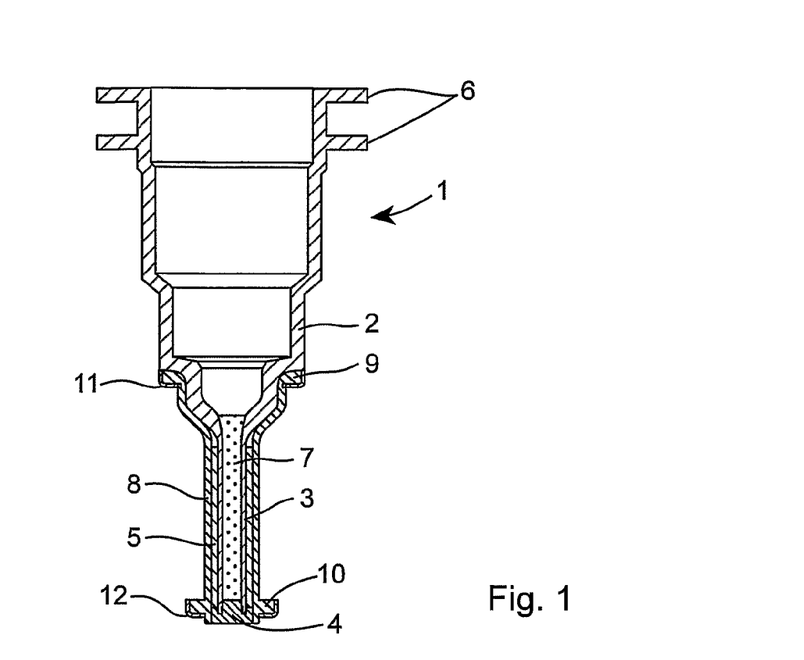
FIG. 1 shows a section through a first embodiment of a reaction vessel according to the invention.

The reaction vessel shown in FIG. 1 is of the same general type as those described in for example WO2005/019836, which is intended for use in an apparatus for conducting a PCR reaction.

The vessel comprises a plastics body (1) with an upper sample receiving portion (2) with a relatively wide mouth so that reagents can, with ease, be added. In the illustrated embodiment, the upper portion includes projecting flanges (6) which are able to interact with a lifting arm in an apparatus such as that described in WO 2005/019836 so as to allow the vessel to be moved in an apparatus adapted to carry out reactions automatically.

At the lower end of the sample receiving portion (2), the vessel terminates in a capillary tube (3) which is sealed at the lower end by a transparent seal (4), forming a transparent window, so as to form an elongate thin reaction vessel, which can contain relatively small sample (7) within the capillary section.

An aluminium coating layer (5) surrounds the capillary tube (3) and is in close thermal contact with it. This coating layer (5) acts as a thermal shunt, which is able to rapidly dissipate thermal gradients which build up along the tube (3) and thus within a sample (7) which is subject to heating and/or cooling. The outer surface of the aluminium coating layer (5) has been anodised so as to produce an insulating layer thereof. In an alternative embodiment however, the outer surface of the aluminium coating layer (5) is coated with parylene to provide electrical insulation.

Figures 3, 4:
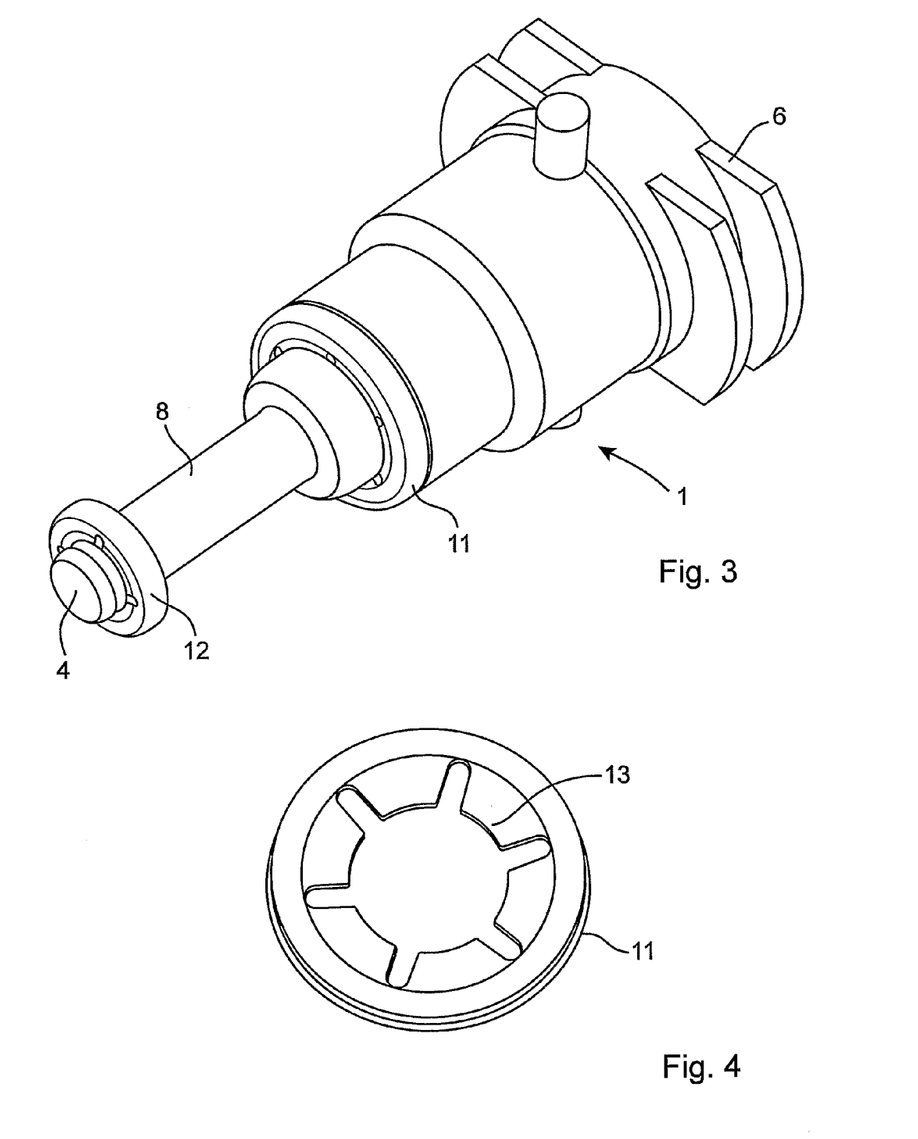
FIG. 3 is a perspective end view of the reaction vessel of FIG. 1.
FIG. 4 shows an electrical connection used in the embodiment of FIG. 3.

An ECP layer (8) completely encases the aluminium coating layer (5) as well as the sides of the lower seal (4) and the base of the upper portion (2). Is it provided with upper and lower ridges (9, 10) respectively which can accommodate upper and lower annular electrical connectors (11, 12) respectively. Each electrical connector (11,12) is provided with a number of inwardly projecting barbs (13) (FIGS. 3 and 4) which are able to pierce the surface of the ECP to ensure that electrical contact is made with the body of the ECP.

In use, this particular vessel can be loaded with sample and PCR reagents, as described in WO 2005/019836. A prepared sample (7) to which has been added all the reagents necessary for carrying a PCR reaction is placed in the upper portion (2) and if necessary a cap (not shown) is placed over open end.

The entire vessel is then centrifuged to force the sample (7) into the capillary tube (3) section of the vessel.

In an alternative embodiment however, the sample and the reagents may be loaded directly into the capillary tube (3) using a specifically designed fine tipped pipettor, and with accompanying close control of pipettor removal, as described and claimed in a copending British patent application of the applicants of even date to the present application.

The vessel is then suitably positioned in an apparatus (FIG. 5) able to accommodate it such that the connectors (11, 12) are connectable to an electrical supply but seat on a pair of supports.

Figure 5:
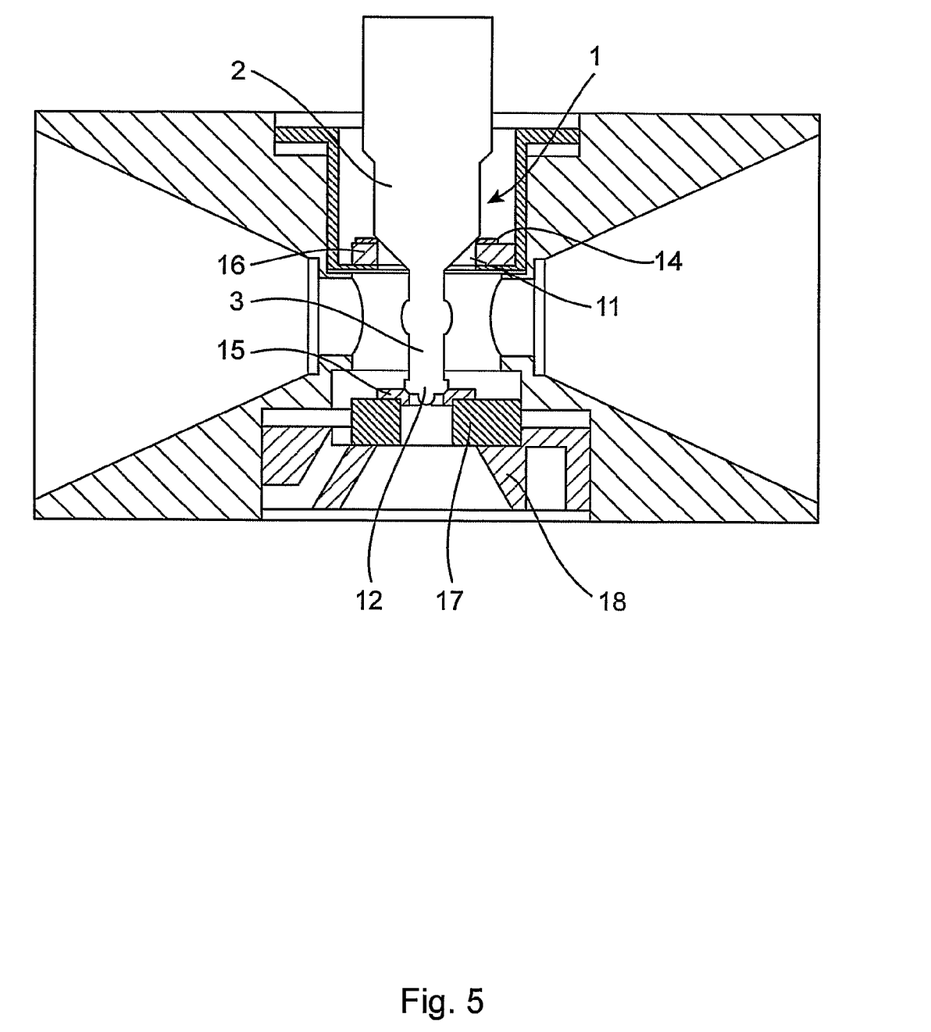
FIG. 5 is a schematic diagram showing a vessel as shown in FIG. 1 in position in a first embodiment of a thermal cycling apparatus.

A ring of a solid foam insulator material (14) (a polyurethane engineering foam) is provided in contact with the lower edge portion of the upper electrical contact (11). The lower electrical contact (12) is held on a shaped support (15), also of the solid foam insulator material.

The solid foam insulator material is arranged to minimise heat transfer from the electrical contacts, but does not interfere with the contact to the electrical supply (not shown).

A ring (16) of solid insulator material such as Delrin is provided adjacent the ring of solid foam insulator material (14) in contact with it. The ring (16) effectively surrounds the rest of the upper electrical contact (11) but is not in direct contact with it. As a result, it acts as an insulator from environmental effects coming from above, but does not act as either a heat sink or heat source in relation to the electrical contact itself.

Similarly, the shaped support (15) of a solid foam insulator material is itself supported on a ring (17) of solid insulator material such as Delrin so as to provide similar protection for the lower electrical contact (5). The solid insulator rings (16, 17) are provided with conduits for electrical connection and spring-mounted in housing (18).

In use, the solid insulator rings (16, 17) combined with the apparatus in which the vessel is held define a chamber for the tube (2) that is effectively isolated from the environment. However, the electrical contacts themselves are in contact with the solid foam material of low thermal mass.

When arranged in this way, the apparatus could be utilised in a polymerase chain reaction in a far more effective and reliable manner, as compared to devices which had no or alternative arrangements of insulator material.

The connectors (11,12) are then connected to the electrical supply, which is controlled, suitably automatically, to pass current through the ECP layer (5) so it rapidly progresses through a series of heating and cooling cycles, ensuring that the sample is subjected to similar cycling conditions. This will allow the sample (7) to be subjected to a PCR reaction.

Where a real-time monitoring system is included in the sample (7), the progress of the PCR can be monitored through the seal (4) using conventional methods.

As a result, rapid PCR can be achieved. The presence of thermal gradients within the vessel (1) and therefore the sample (7) is reduced by the measures taken, including in particular the presence of the aluminium coating layer (5) which acts as a thermal shunt. Thus reliable and reproducible results may be achieved.

Figure 2:
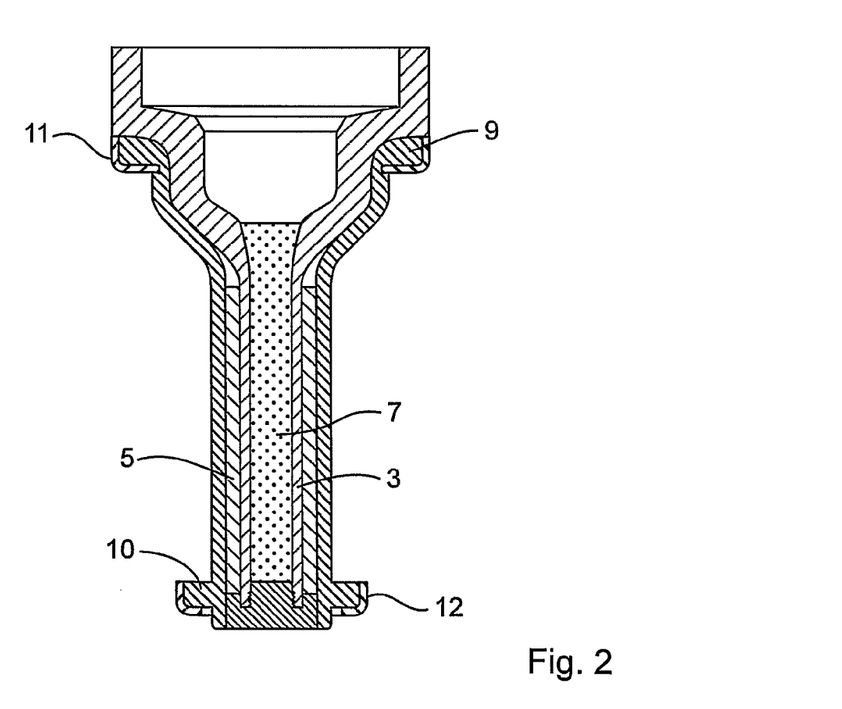
FIG. 2 shows an enlarged view of the portion of the reaction vessel shown in FIG. 1, which incorporates the elements of the invention.
Figure 6:
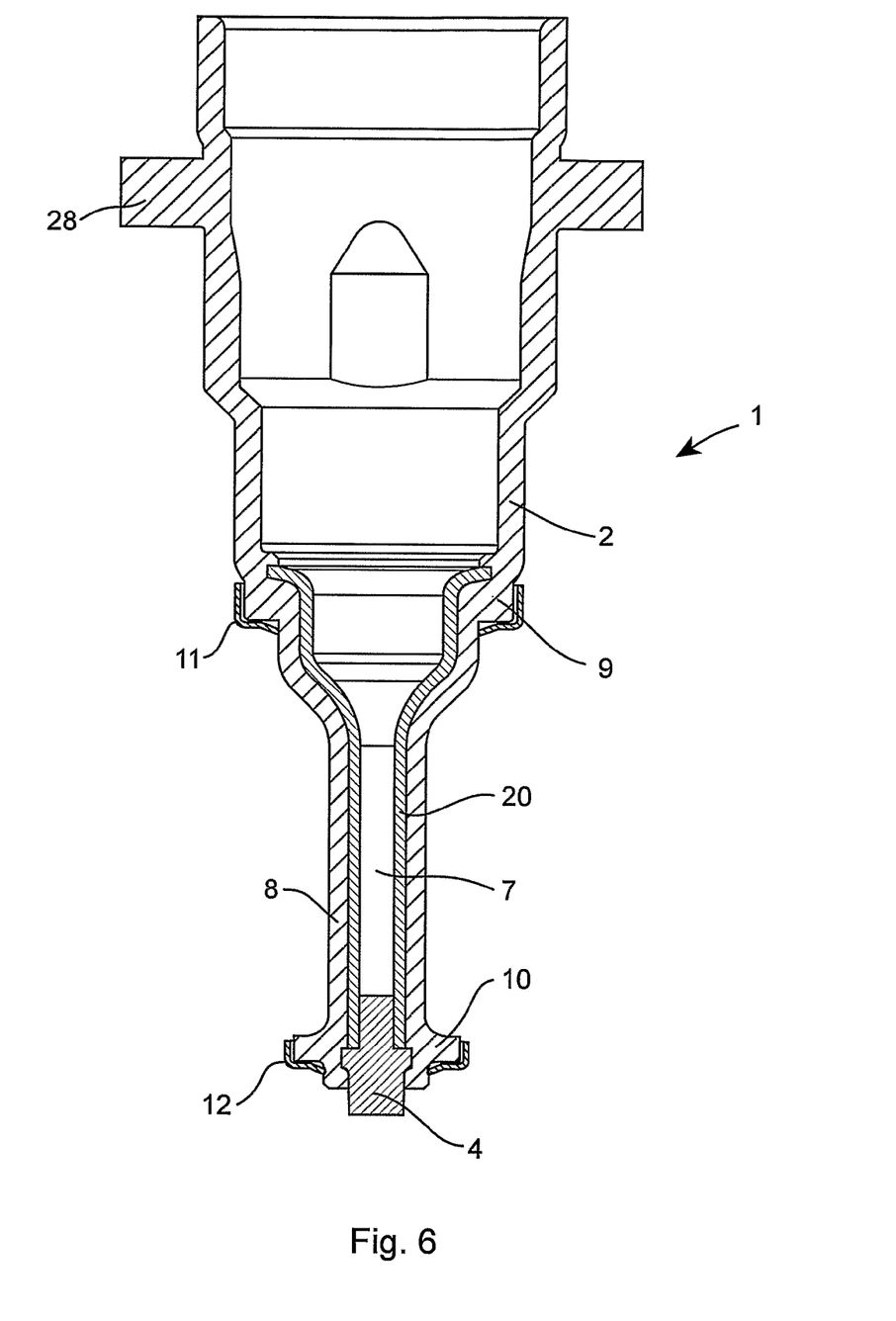
FIG. 6 shows a section through a second embodiment of a reaction vessel according to the invention.

An alternative design of sample vessel is illustrated in FIG. 6. Many of the features are the same as illustrated in FIGS. 1 and 2 and use the same reference marks.

The upper body (2) is similar to the embodiment illustrated in FIG. 1 and will not be described in any more detail. The view shown in FIG. 6 shows two protruding lugs (28) which are able to interact with sockets allowing the vessel to be centrifuged. In this embodiment, the capillary tube (20) is made from aluminium. The aluminium capillary tube (20) is anodised and coated with parylene. The anodised layer provides electrical insulation, whilst the parylene layer provides biocompatibility (and also assists with electrical insulation).

The transparent window (4) is inserted into the end of the aluminium capillary tube (20), which is held in place by an interference fit. The transparent window (4) is made of polycarbonate, preferably Makrolon™ which has sufficient rigidity to enable the window to be inserted into the capillary and is transparent to enable optical monitoring of the sample. The transparent window is provided with a silicon O-ring which, when the transparent window is in place, is positioned against a chamfered edge of the capillary tube, ensuring a good seal. This O-ring is made of silicon overmoulded onto the polypropylene window. The transparent window extends some distance into the capillary tube by 1-1.5 mm. This is advantageous because the area at the bottom of the capillary tube adjacent the edge of the ECP is the area of highest temperature gradient. By filling this area with the transparent window, the sample is placed away from the end of the aluminium capillary tube (20) and ECP (8), in an area of low temperature gradient.

Once the transparent window is inserted into the capillary tube, the capillary tube is overmoulded with ECP (8). The end of the window is free of ECP, so that it remains transparent.

Figure 7:
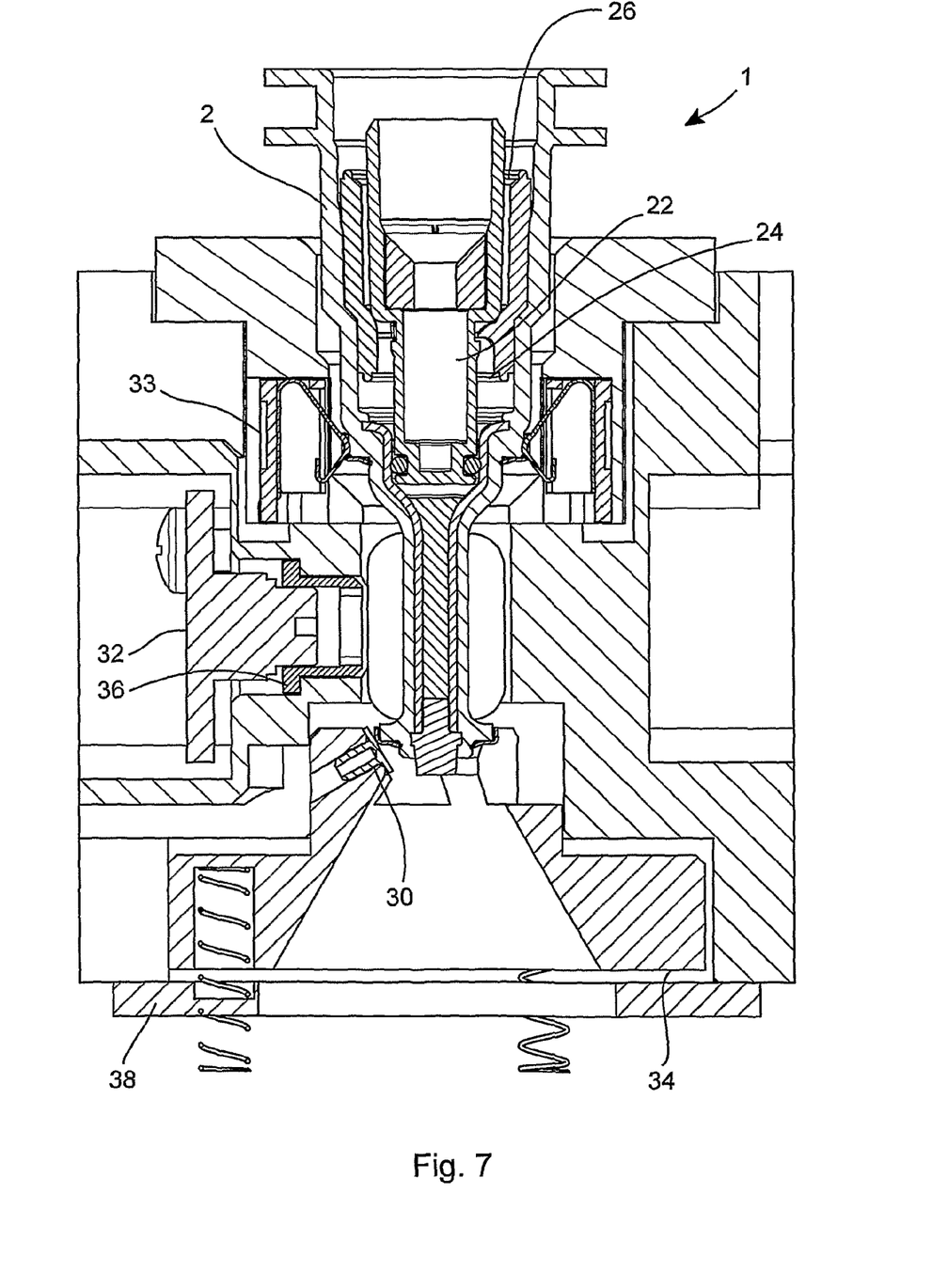
FIG. 7 is a schematic diagram showing a vessel as shown in FIG. 1 or 6 in position in a second embodiment of a thermal cycling apparatus.

FIG. 7 shows an alternative embodiment of the apparatus illustrated in FIG. 5. The sample vessel (1) is shown inserted into the apparatus. The sample vessel is held in position by three upstanding mounts (30) (only one shown). These mounts have low thermal mass due to their low volume and low thermal conductivity. In this embodiment the mounts are made of black Delrin. The mounts (3) are retained in a bottom contact retainer (34) which is in turn sprung mounted onto a bottom plate 38.

Upper electrical contacts 33 are in the form of metal springs which brush against the upper electrical connection of the vessel. A lower electrical contact is incorporated into one of the upstanding mounts (30). The upper and lower electrical contacts have low thermal mass due to their low volume.

FIG. 7 also shows a thermopile (32) for sensing the temperature of the ECP through a vertical slit (36) which has a field of view configured to view the ECP layer of the vessel with minimal interference from other parts of the apparatus.

FIG. 7 also shows a cutter/stopper (22) in the upper section of the vessel. Also shown are two ruptured seals (24),(26) which have been pierced by the cutter/stopper. The cutter (22) is moved to pierce the upper and lower seals (24),(26), releasing a reagent or solvent stored between them into the sample vessel. When lowered the cutter/stopper seals the sample vessel. Such a combined cutter and stopper is disclosed in WO2005/019836. The use of the metal capillary tube has the advantage that it forms a good seal with the stopper, as opposed to the stopper being in contact with ECP with which it is difficult to get a good seal.

The invention claimed is:

1. A reaction vessel for conducting a chemical or biochemical reaction, said reaction vessel comprising a capillary vessel or a flattened capillary vessel; and at least one wall of said reaction vessel comprising a thermally conducting layer, an inner non-metallic layer and an integral resistive heating element which is arranged outside the thermally conducting layer; the thermally conducting layer comprising a metallic layer with a passivated outer surface, and wherein the integral resistive heating element is electrically insulated from the metallic layer by the passivated outer surface of the metallic layer.

2. The reaction vessel according to claim 1, wherein said reaction vessel comprises long walls, wherein the one wall forms at least one of the long walls.

3. The reaction vessel according to claim 2 wherein a base of the capillary vessel or the flattened capillary vessel is of a transparent material.

4. The reaction vessel according to claim 3 wherein a seal is provided between the transparent material and the capillary vessel or the flattened capillary vessel.

5. The reaction vessel according to claim 1 wherein an entire side wall of the reaction vessel comprises a metallic layer and an inner non-metallic layer.

6. The reaction vessel according to claim 1 wherein the metallic layer comprises aluminum.

7. The reaction vessel according to claim 1 wherein the inner non-metallic layer is a polymeric material, glass, a passivated metal or a combination of these.

8. The reaction vessel according to claim 7 wherein the polymeric layer comprises a compound of formula (I)

where R is a substituent group selected from $R^1$, $OR^1$, $SR^1$, $OC(O)R^1$, $C(O)OR^1$, hydroxyl, halogen, nitro, nitrile, amine, carboxy or mercapto and where $R^1$ is any hydrocarbon group and where $R^1$ may be optionally substituted by one or more groups selected from hydroxyl, halogen, nitro, nitrile, amine or mercapto; and where m is 0 or an integer of from 1 to 3; and n is sufficient for the compound to be a polymer.

9. The reaction vessel according to claim 1 which is adapted for use in a block heater.

10. The reaction vessel according to claim 1 wherein the integral resistive heating element comprises electrically conducting polymer.

11. The reaction vessel according to claim 10 which further comprises a barbed electrical contact which pierces a surface of the electrically conducting polymer and is connectable to a control system which allows controllable heating of the electrically conducting polymer.

12. The reaction vessel according to claim 10 wherein a radial thickness of the electrically conducting polymer varies along the reaction vessel so as to reduce thermal gradients therealong.

13. The reaction vessel according to claim 1 wherein the passivated outer surface of the metallic layer comprises a layer of anodized aluminum.

14. The reaction vessel according to claim 1 wherein the passivated outer surface of the metallic layer comprises a polymer layer.

15. The reaction vessel according to claim 14 wherein the polymer layer a compound of formula (I)

where R is a substituent group selected from $R^1$, $OR^1$, $SR^1$, $OC(O)R^1$, $C(O)OR^1$, hydroxyl, halogen, nitro, nitrile, amine, carboxy or mercapto and where $R^1$ is any hydrocarbon group and where $R^1$ may be optionally substituted by one or more groups selected from hydroxyl, halogen, nitro, nitrile, amine or mercapto; and where m is 0 or an integer of from 1 to 3; and n is sufficient for the compound to be a polymer.

16. A reaction system comprising a reaction vessel according to claim 1, and an apparatus which accommodates said reaction vessel, and the apparatus comprises a heating system adapted to controllably heat and cool said reaction vessel.

17. The reaction system according to claim 16 wherein the heating system is an induction heating system, able to interact with the metallic layer of the reaction vessel so as to heat it by induction.

18. The reaction system according to claim 16 wherein the heating system supplies heated fluid to the reaction vessel or a vicinity thereof, so as to effect heating, and is also able to supply non-heated fluid to the reaction vessel or the vicinity thereof, so as to effect cooling.

19. The reaction system according to claim 18 wherein the heated fluid is air.

20. The reaction system according to claim 16 wherein the heating system is connected to the integral resistive heating element.

21. The reaction system according to claim 20 wherein the apparatus comprises a solid foam material arranged in direct contact with at least one electrical connector of the integral resistive heating element.

22. The reaction system according to claim 21 wherein the foam material is a honeycomb or reticulated foam.

23. The reaction system according to claim 21 wherein the foam material forms a pillared or corrugated mount for the electrical connector.

24. The reaction system according to claim 16 wherein the apparatus is able to accommodate multiple reaction vessels.

25. A method for carrying out a chemical or biochemical reaction which requires at least one heating step, said method comprising placing chemical or biochemical reagents into said reaction vessel according to claim 1 and heating said reagents so as to bring about said chemical or biochemical reaction.

26. The method according to claim 25 wherein the reaction requires thermal cycling.

27. The method according to claim 26 wherein the reaction is a polymerase chain reaction.

28. A method for carrying out a chemical or biochemical reaction which requires at least one heating step, said method comprising placing chemical or biochemical regiments into the reaction vessel of the reaction system according to claim 16 and heating said reagent so as to bring about said chemical or biochemical reaction.

* * * * *